United States Patent [19]
Fritz

[11] Patent Number: 5,260,219
[45] Date of Patent: Nov. 9, 1993

[54] METHOD OF DETERMINING NITROGEN BALANCE AND FAT LOSS FOR PERSONS INVOLVED IN DIET AND/OR PHYSICAL TRAINING PROGRAM

[76] Inventor: Robert Fritz, P.O. Box 1948, Martinez, Calif. 94553

[21] Appl. No.: 751,157

[22] Filed: Aug. 28, 1991

Related U.S. Application Data

[63] Continuation-in-part of Ser. No. 625,866, Dec. 11, 1990, Pat. No. 5,137,692.

[51] Int. Cl.$^5$ .................... C01N 21/78; C01N 33/493
[52] U.S. Cl. ........................ 436/71; 436/106; 436/108; 436/169; 436/114; 436/128; 436/130; 436/805; 436/810; 436/811; 435/4; 435/12
[58] Field of Search ............... 436/106, 108, 114, 128, 436/130, 164, 71, 169, 805, 807, 808, 810, 811; 435/4, 7.1, 12

[56] References Cited

U.S. PATENT DOCUMENTS 3,531,254  9/1970  Okuda ................................ 436/108
5,071,769 12/1991  Kundu et al. ...................... 436/128

OTHER PUBLICATIONS

Fritz, R. Journal of Sportscience, 1986, pp. 1-7.
J. Fraser, Marion C. Fetter, R. L. Mast and A. H. Free; "Studies With Simplified Nitroprusside Test For Ketone Bodies in Urine Serum, Plasma, and Milk", *Clinica Chemica Acta;* May 19, 1964; pp. 372-377.
Peter Paterson and June Sheath; "Material and Foetal Ketone Concentrations in Plasma and Urine"; *The Laucet;* Apr. 22, 1967; pp. 862-864.
Ames (Product Flier); "Keostix ® Reagent Strips"; 1984; one page only.
Frank L. Engel and Thomas T. Amatruda; "Hormovan Aspects of Ketosis"; *Annals New York Academy of Sciences;* 1963; pp. 753-771.
Williamson, D. H.; "Phsiological Ketosis, or Why Ketone Bodies"; *Postgraduate Medical Journal;* Jun. Suppl. 1971; pp. 371-375.
Mark A. Tarnopolsky, J. Duncan MacDougall, and Stephanie A. Atkinson; "Influence of Protein Intake and Training Status on Nitrogen Balance and Lean Body Mass"; *American Physiological Society;* Aug. 17, 1987; pp 87-193.

*Primary Examiner*—James C. Housel
*Assistant Examiner*—David Redding
*Attorney, Agent, or Firm*—Bielen, Peterson & Lampe

[57] ABSTRACT

A test kit for determining the relative level of nitrogen of a user who is involved in a health program where diet and exercise are monitored and adjusted for optimizing physical development, the system includes a plastic stick having a first reagent zone on which is included a reactant such as urease, and a pH indicator such as bromthymol blue, and a second reagent zone on which is included a reactant indicator such as sodium nitroprusside used in conjunction with color chart blocks representing a range of urea nitrogen and ketone concentrations, wherein the user's urine nitrogen and ketone content can be determined by comparing the altered color of the reagent zone of an exposed test strip to the color chart blocks and compared with a personal baseline level, developed from a number of tests under controlled conditions, for determining the present protein nitrogen turnover and approximate balance, and the body fat metabolism.

5 Claims, 2 Drawing Sheets

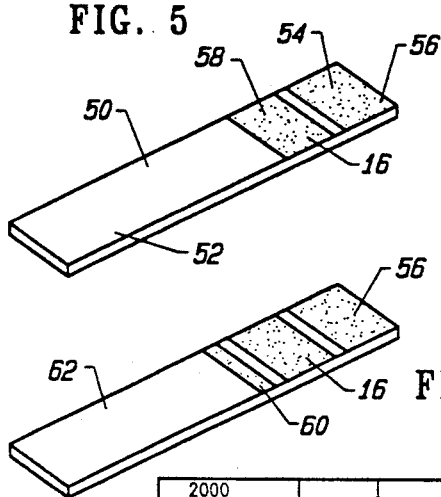
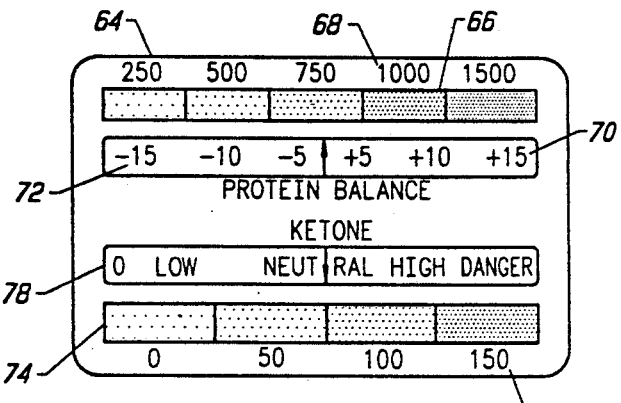
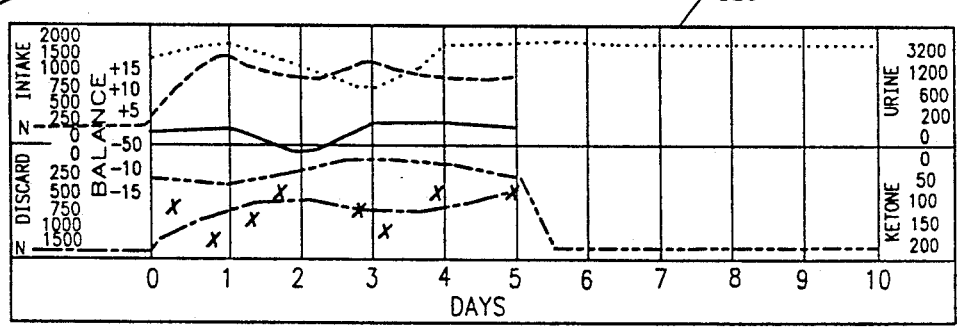
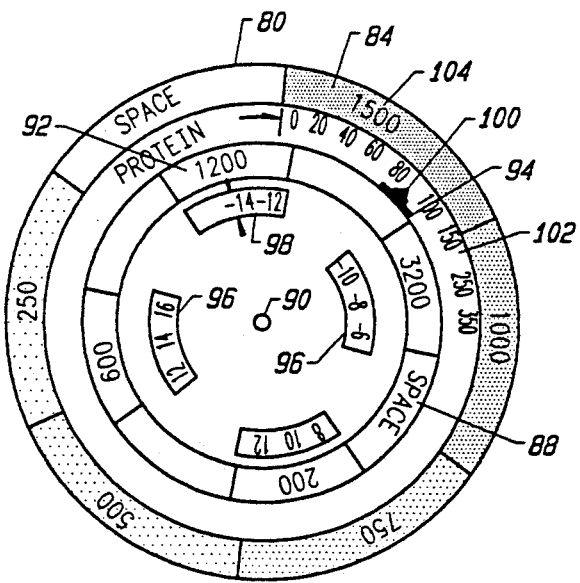
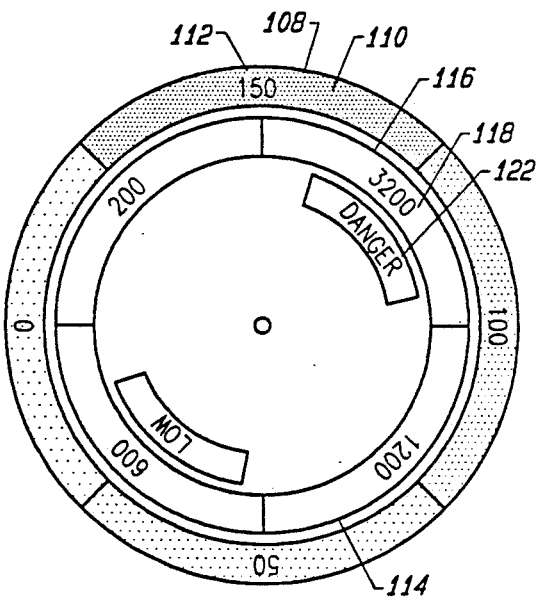
FIG. 5
FIG. 6
FIG. 7
FIG. 10
FIG. 8
FIG. 9

METHOD OF DETERMINING NITROGEN BALANCE AND FAT LOSS FOR PERSONS INVOLVED IN DIET AND/OR PHYSICAL TRAINING PROGRAM

BACKGROUND OF THE INVENTION

This invention is a continuation-in-part of application Ser. No. 625,866, filed Dec. 11, 1990, now U.S. Pat. No. 5,137,692, entitled, "Nitrogen Test Kit for Physical Training."

This invention relates to a non-invasive field kit to permit self-determination of the relative level of a chemical agent in the urine of a person, particularly a person involved in a health program. In particular, the invention relates to a means to self-test urine using a disposable, indicator test strip having an impregnated reagent area for estimating the amount of urea nitrogen and in a preferred embodiment the level of both urea nitrogen and ketones, in the urine for determination of the fat loss and nitrogen balance of a person in a dietary and physical exercise program.

The majority of people who go on diets gain back all lost weight within 12 months. The typical diet causes rapid weight loss but the results are usually unsatisfactory to the dieter. Usually, 30-40 percent of lost weight is from the lean body mass (fat-free weight, largely muscle). Often, the person looks gaunt from lack of muscle tone and has little energy. Weight losses have been illusory; only a portion of the decreased body weight has been from fat. A significant portion of the loss has been from muscle mass, the part of the body composition that gives the body shape and form. The real goal of dieters is to look better. To do this they must lose fat and maintain or gain muscle mass.

The rate that weight is lost will determine the success of the program. If weight is lost too quickly using starvation diets, then the body will use its muscle for energy and lean body mass will decrease. If the diet is not stringent enough, then no progress will be made. People need a way of determining if they are losing weight at a rate that will give them the results they want.

The ketone test program coupled with a nitrogen test program can help people gauge the ideal rate of weight loss. The combination sticks allow the dieter to determine, at home, if body protein is being used for fuel and if fat stores are decreasing at the ideal rate. This is accomplished by measuring the concentrations of urea nitrogen (UN) and ketone bodies (KB) in the urine.

Urea nitrogen is a by-product of amino acid metabolism. If UN is greater than the nitrogen consumed in the diet, then the body is using its own protein for energy. By performing a simple urine UN test, dieters know instantly if they are losing weight by depleting their fat stores or wasting their muscles for energy.

Ketone bodies (acetoacetic acid, B-hydroxybutyric acid, and acetone) are formed from the breakdown of fatty acids, the principle component of body fat. Ketones increase during starvation and are a good measure of the rate that body fat is being used. If ketones are too high, then the dieter is in danger of losing weight too rapidly.

Combining the measurement of urea nitrogen and ketones will give the dieters what they want: fat loss without sacrificing muscle mass. The procedure is simple, easy to interpret, and medically viable. If used with a sensible diet and exercise program, it will combine proven urine chemical procedures, adapted to home use, with a sensible and healthy weight loss technique.

This procedure provides a more gradual and permanent way to lose weight that will promote health and provides a plan that causes desirable weight changes and contributes to the well-being and attractiveness of the user.

It has been recently recognized that the rate at which an individual absorbs and excretes nitrogen is a good indicator of the individual's nutritional health. Particularly when an individual is involved in a program requiring both dietary control and physical activity, the "nitrogen balance" is considered to be critical in determining whether the individual will have a net physiological gain or loss from a particular physical session.

Nitrogen balance is a term used to define whether an individual is experiencing a net gain or loss in nitrogen, in the form of protein, as a result of his food intake and activity level. Useable nitrogen is added to the body through consumption of protein. Nitrogen is eliminated from the body through various pathways such as urine, feces, perspiration, menstruation and respiration. Other particular situational phenomena can add to normal losses, such as calorie reduction, injury, stress, heavy physical training, profuse sweating and abnormally low quality or quantity of protein intake. As heavy physical training is one known method of substantially altering the body's requirement for nitrogen in the form of dietary amino acids, it is desirable that anyone involved in strenuous athletic activity or in physical training, be conscious of his metabolic rate, and be particularly conscious of the assimilation, utilization and elimination of nitrogen compounds.

Similarly, anyone involved in a dietary program for weight reduction should be conscious whether the diet is causing weight loss by the burning of body fat and not by the cannibalization of muscle mass. It should be emphasized that a proper weight loss program must combine a dietary regime with an exercise program to maintain muscle activity and preferably to promote muscle increase concurrent with fat loss. Such a dietary regime must therefore include an appropriate supply of amino acids in the form of protein to insure that the body has an adequate amino acid supply to maintain current muscle mass and preferably promote muscle increase.

Unlike plants which can assimilate nitrogen from fertilizers and in certain cases directly from the air itself, a human is totally dependent upon protein for the daily requirements of nitrogen. The various amino acids that form the intake proteins are utilized for the resulting synthesis of body proteins. Synthesized proteins find their way into the formation of virtually all of the body's tissues, including most prominently muscle tissue, but also in hair, organs and to one degree or another almost in every other particle of the human body. When there is an equilibrium nitrogen balance, the proteins taken in by an appropriate diet replace those proteins that are metabolized or discarded on a daily basis. Dietary protein, therefore, is a critical factor in maintaining a nitrogen balance. Utilization of body protein during the process of athletic training, particularly strenuous activities such as weight training, can also affect the protein balance. Exercise leads to enhanced metabolization of both protein and available carbohydrates.

Clinical methods of determining the urea content and hence nitrogen content of whole blood and plasma have been developed. Furthermore, a reagent strip test method for estimating urea content of whole blood simplifies the test procedure and provides a useful screening test for uremia. The reagent strip test, however, requires at least one or two drops of blood and is therefore an inconvenient method for regular and repetitive testing, particularly for self-testing under less than antiseptic conditions.

Reagent strips such as pH indicators are a known means of providing a convenient method to approximate the acidity or alkalinity of a solution. The urea content of bodily fluids can be detected by reacting the urea with urease which catalyzes the hydrolysis of urea to carbon dioxide and ammonium hydroxide. The ammonium hydroxide quantitatively increases the pH of the solution and this increased pH is measured by color change of a pH sensitive indicator, such as bromthymol blue.

In a similar manner the excretion of acetoacetic acid in the urine provides a means for indicating carbohydrate and fat metabolism. While urine test strips have been developed for diabetics to alert the physician and diabetic to changes in condition that may warrant changes in diet or medication, such test strips have not been incorporated into a dietary program for monitoring the effectiveness of a dietary regimen in loss of body fat without loss of muscle mass. A reagent, such as sodium nitroprusside reacts with a ketone in the urine, typically acetoacetic acid to form a purple complex with the reagent. A reagent color change from pink to shades of increasingly dark purple provides a rough quantitative measure of ketones in the urine stream.

In the preferred use the ketone test is combined with the nitrogen test to monitor the fat loss along with nitrogen metabolism to insure a healthy diet is being implemented. An ineffective starvation diet will be indicated by a rise in the ketone level and a negative protein balance signaling an improper diet deficient in protein and/or calories.

In modern health programs it is an objective to promote controlled body shaping. Although past invasive systems are inappropriate for the purposes proposed, this invention devises a means for adapting and utilizing the reagent strip screening test for monitoring ketone level and nitrogen turnover or approximate balance, enabling a user to adjust his diet and exercise program according to quantitative results of convenient, self-administered urine tests. The urine tests are compared to a personal baseline for each measure developed by following a test regimen whereby the user is able to determine whether he or she is in a state of protein surplus or deficiency. Coupled with the ketone test using the ketone test strip or a preferred combination nitrogen/ketone test strip the user is able to determine whether active fat metabolism is occurring at a time when muscle mass is being maintained or increased. For a truly effective health program where loss of body fat is desired, muscle mass must be maintained, and preferably increased to provide a healthy physique and sense of well-being that is based on actual physical condition, not perceived appearance.

SUMMARY OF THE INVENTION

This invention relates to a system for determining the nitrogen turnover and ketone status of a user who is involved in a health program where diet, exercise or both are monitored and adjusted for optimizing physical development. Since urea is predominantly discharged from the body through urine (90%), testing the urea content of urine provides a non-invasive manner of determining the relative level of urea nitrogen in the system. Fluctuations in the urea content under controlled conditions can provide a quantitative method of determining the effect of emphasized factors in diet and training.

By use of a simple quantitative test indicator, a training athlete or dieter can tailor his dietary and exercise program to maximize the body's protein utilization and minimize those situations where excess training or dieting may be deleterious to bodily development. The non-invasive indicator system of this invention comprises a kit including a plastic stick having one or more reagent zones on which is included a reactant and indicator. For example, for the nitrogen test the reactant is urease, and the indicator is a pH indicator such as bromthymol blue. By the use of color chart blocks representing a range of urea nitrogen concentrations, the user's urine nitrogen content can be personally determined by comparing the altered color of the reagent zone of an exposed test strip to the color chart. The indicator system can be adapted to include additional reagent zones for determining ketone status and other nutritional status, such as vitamin, hormone or metabolite states, by appropriate reactants and color indicator means.

In nitrogen tests, a single sampling for nitrogen level will not provide sufficient basis for determining the nitrogen balance of the tested user. However, repetitive sampling under controlled conditions can establish a general personal level from which deviations can be detected that are indicative of changes in diet or training variables such as intensity, frequency and duration. As the test method is non-invasive, and can be accomplished in a simple procedure during normal urination with a discardable implement, repetitive sampling is a minimal burden. The system, while primarily used for human use is adaptable for use with animals, particularly those involved in strenuous training programs such as race horses, greyhounds and sled dogs.

Clinical methods of determining nitrogen balance require complex and exact determination of nitrogen intake and nitrogen discharge. Nitrogen intake is almost exclusively a factor of dietary intake of useable protein. Nitrogen loss is primarily in the form of eliminated urea. Urea is measured in excreted urine, feces and perspiration. Other nitrogen losses, such as protein discarded as hair loss during shaving, blood loss during menstruation and other nitrogen losses must be carefully measured. The nitrogen balance is determined by comparing the nitrogen intake with the nitrogen loss over a defined period of time.

In a similar manner, the relative nitrogen balance can be determined by detecting the level of nitrogen excreted in the urine. While the level of nitrogen loss for various pathways may vary according to individuals, the quantitative measurement of the nitrogen level in the urine can provide an approximate indicator as to the current state of the individual when compared with a personal baseline developed by controlled measurements over a period of time. Urea content of the urine measured during relatively nascent periods of exercise with normal dietary habits can establish a preliminary baseline. Moderate variations in exercise and diet, including dietary supplements, can assist in establishing a reliable personal baseline. Once the personal baseline is determined, deviations from the baseline as a result of defined activities can be detected to determine whether the individual is in a positive state (anabolic), a negative state (catabolic), or a state of equilibrium. The degree of deviation from the baseline as a result of defined activities can provide a clear indication of the state of approximate nitrogen balance, that is, a balance, or, the level of imbalance. As the user becomes more practiced, the baseline can be confidently adjusted to more accurately reflect the actual state relative to equilibrium. Fewer tests are subsequently required to detect deviations and determine physical state.

Where a trainee is involved exclusively in a weight loss program, a ketone test strip can be used in conjunction with a reference chart to determine the level of fat metabolism. Where diet is controlled, the level of fat metabolism can be compared with a base line level to determine if excess ketone production signals a detrimental diet regime. Preferably the ketone test strip is used in conjunction with a nitrogen test strip or in a combination stick having a nitrogen test reagent and indicator to insure that a proper nitrogen balance or better, an anabolic condition is being maintained.

The purpose of the ketone test strip is to monitor the rate of weight loss to insure fat is lost while lean body mass is maintained. If weight loss is too rapid and the weight loss program is structured incorrectly, then body protein is lost and the concentrations of ketones in the blood and urine increase markedly. In the ideal weight loss program, the dieter should be in nitrogen balance with little or only slightly elevated levels or urine ketones. Negative nitrogen balance and elevated ketones in the urine suggests that the dieter is losing weight too quickly. He or she is losing muscle mass and creating an unhealthy internal chemical environment. The normal range or urinary ketone excretion is 3015 mg. per 24 hours. Calculating 24 hour ketone (as acetone) excretion is very similar to the technique used to measure urine urea nitrogen. Measurements are taken using the ketone strip and value is extrapolated to 24 hours.

For a more accurate determination of nitrogen balance and ketone level, a regimen measuring all urine discharge over a set period with strict monitoring of diet is preferred as described hereafter.

In order that the indicator system be practical for use in diet programs or athletic training, it must be non-invasive and convenient to perform. The use of a wetable and discardable indicator stick having a reagent strip thereon that can be passed through a urine stream during normal urination for immediate visual detection and subsequent discard incorporates these features. When coupled with a convenient comparison chart and procedure for determining the user's baseline and health line, the test kit provides a quantitative means for determining the effect of diet and exercise in a diet, health, or fitness program. As additional factors in nutritional health become quantifiable by self-administered urine tests, other reagent zones can be added to the test strip to determine nutritional states, for example vitamin or hormone levels or warning lines, for example where steroid or drug use is detectable.

BRIEF DESCRIPTION OF THE DRAWINGS

FIG. 5 is a perspective view of a combination test stick.

FIG. 6 is a perspective view of an alternate embodiment of a combination test strip.

FIG. 7 is a plan view of a color code card.

FIG. 8 is a front view of a frontside of a calculating wheel for nitrogen tests.

FIG. 9 is a back view of an obverse side of a calculating wheel for ketone tests.

FIG. 10 is a plan view of a health line chart.

DESCRIPTION OF THE PREFERRED EMBODIMENTS

Figure 1:
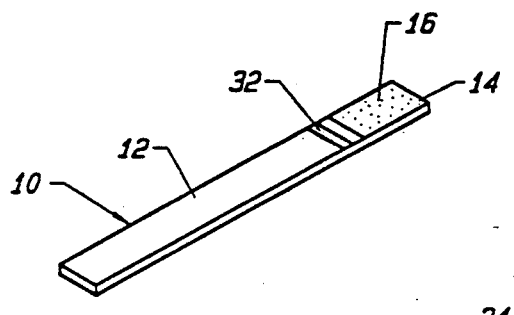
FIG. 1 is a perspective view of a nitrogent test stick.

The non-invasive indicator system of this invention is directed at determining the relative level of approximate nitrogen turnover, nitrogen balance of an individual, particularly an individual engaged in a dietary or exercise program and most specifically in a health and fitness program with attention to both diet and exercise. In the preferred embodiment, the indicator system includes a combination test system for determining relative nitrogen levels and ketone levels in urine for physical conditioning where fat loss and muscle gain are important objectives. The indicator system comprises a simple field test method combined with diet programs and athletic training programs where both exercise and dietary regimens are deliberately regulated to maximize the positive effect of the programs. The indicator system is designed for human use, but is adaptable to animal use, particularly for training programs involving speed or endurance.

While a number of factors directly influence the nitrogen balance and ketone level, predominant factors are the quantity and quality of amino acids consumed in the form of dietary protein, the restriction of carbohydrate, fat and saturated oils from the diet, the caloric content of the diet and the intensity, duration and frequency of the physical training regimen. Intense physical exercise can result in a hypermetabolic state that elevates an individual's energy requirements to three times as high as a basal state. This can result in a catabolic or protein deficient state in which the body responds by utilizing its own amino acid supply resulting in fatigue and muscle cannibalization. Similarly, severe dieting without exercise and protein intake can also result in a catabolic state with weight loss in substantial part caused from loss of muscle mass and an unhealthy condition prone to weight gain without full replacement of lost muscle mass.

While elaborate quantitative tests can be performed to precisely determine the nitrogen balance of an individual, the procedure requires the exact cataloging of the amino acid intake including the type of protein and its utilization factor, that is, the measure of the effectiveness in which the body can utilize that particular type of protein. Nitrogen loss, through the various pathways previously enumerated, must also be quantified. Intake and loss must then be compared to determine the surplus or deficiency during the period measurements are performed.

This invention provides a personal system for an individual to establish his own baseline level of approximate nitrogen turnover and balance, and, by a controlled diet and measured urine program to determine the state of his nitrogen balance and level of fat loss by a simple, non-invasive test. This invention in its most effective embodiment combines a personal system for an individual to establish his baseline level of approximate fat metabolism and to determine that fat loss is occurring during a conditioning program particularly where the program includes an exercise regimen designed to increase muscle and fat loss where fat loss would otherwise be masked by no weight change or weight increase due to added muscle.

As shown in FIG. 1, an indicator stick or detection wand for nitrogen, designated generally by the reference numeral 10 is fabricated from a plastic strip 12 with a reagent area or zone 14 at one end of the strip having a chemical reagent 16 thereon that reacts with urine to indicate the level of nitrogen in the specimen of urine tested. The reactive ingredients of the reagent are urease and bromthymol blue under a permeable membrane. The urease reacts with the urea in the urine to hydrolyze the urea to carbon dioxide and ammonium hydroxide. The liberated ammonium hydroxide increases the pH of the specimen and the shift in alkalinity is indicated by the change in hue of the bromthymol blue. To achieve the range desired, the reagent zone is impregnated with 3.2 I.U. of urease and 33 mcg. bromthymol blue. A non-reactive yellow dye is added to the reagent to provide a convenient color scale change from yellow through green to dark blue-green for comparison with a color block grid.

Figure 2:
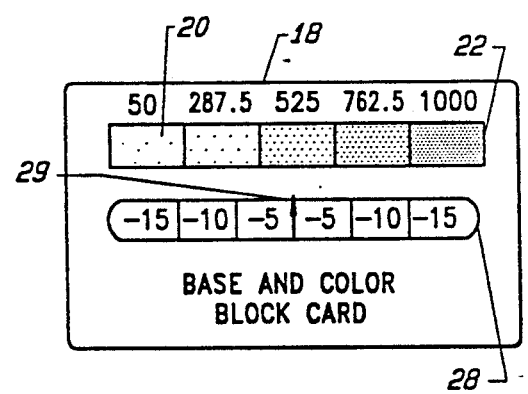
FIG. 2 is a plan view of a color code card with nitrogen color chart blocks.

As shown in FIG. 2 a convenient wallet-size card 18 includes a series of color blocks 20 forming a color block grid 22 having hue variations that are calibrated in range steps of 50, 287.5, 525, 762.5 and 1000 to indicate milligram quantities of urea nitrogen per decaliter of urine sample. For weight training where higher anabolic states are desired a grid having hue variations that are calibrated in range steps of 250, 500, 750, 1000 and 1500 are preferred.

The color block chart is calibrated to define the current level of nitrogen in the urine sample. By careful repetition of a recommended test procedure, a reasonable accuracy can be established in measuring the level of nitrogen in the urine specimen.

In order for the user to have a comparative means to determine whether the tested level of urea nitrogen conforms to an anabolic or catabolic state, the user must establish a baseline representing the balanced state. To establish a personal baseline, the user records a series of tests performed under relatively constant programs of moderate exercise and preferably normal diet. During the period of establishing the baseline, there should be no overall weight gain or weight loss. As an example, to establish a baseline level of approximate nitrogen balance, a period of at least three days is used for testing. The trainee's urine is tested upon waking (within 30 minutes of waking and before breakfast); before lunch; before moderate exercise (zero to 30 minutes prior); after exercise (one to two hours and before eating); and prior to bedtime (zero to 30 minutes).

The same testing procedure is utilized for each test. The indicator stick 10 is wet at the reagent zone by a urine stream or with a least two drops of urine. The reagent zone is wiped clean with a tissue after 15 seconds of contact. At the end of 60 seconds the color of the reagent area is compared with the color blocks 20 of the reference grid 22 on the chart card 18 and the quantitative level of urine nitrogen read.

To conveniently record each result of the tests, a graph pad 24 having sheets 25 with a reference grid 26 for plotting the test results during the baseline test procedure. After three days of testing, a fourth chart can be constructed using the average of each of the five daily periods. This chart will provide a convenient reference to the normal fluctuations that occur during the day.

To convert the nitrogen level tests to a general protein balance baseline, the average five periods are again in turn averaged to provide a single value signifying the baseline balance point for future reference. This can be provided on a stick-on conversion strip 28 as shown in FIG. 2. The stick-on conversion strip has a center balance arrow 29 that aligns with the appropriate nitrogen level in the color block grid 22 representing the averaged value. The conversion strip 28 is divided into plus and minus segments having values designating the approximate excess or deficiency of protein in grams per day.

Figure 4:
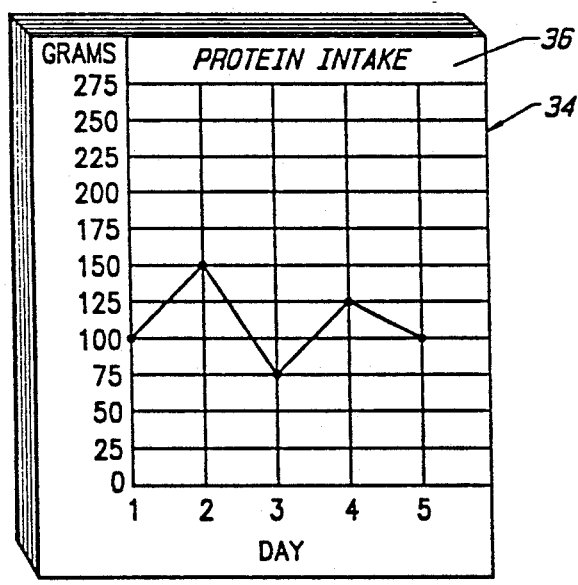
FIG. 4 is a plan view of a diet record pad.

To determine the effects of physical training alterations, the diet should be held relatively constant for five consecutive days while training changes occur. Diet is recorded and listed for nitrogen content on the diet record pad 34 shown in FIG. 4. The diet record pad 34 has sheets 36 with a graph format for recording grams of dietary protein over a five day test period. Fluctuations in nitrogen excretion, relative to nitrogen intake, reflect effects of physical training. Similarly, to determine the effect of dietary alterations, hold the physical training constant for five consecutive days while diet changes take place. Diet is recorded and listed for nitrogen content. Fluctuations in nitrogen excretion, relative to nitrogen intake, reflect effects of the diet. Preferably, for such determinations, the test procedure for determining the baseline, that is, the Phase I procedure, should be utilized. In Phase 2, the test procedure can be reduced to three period during the day: waking (within 30 minutes of waking and before breakfast); before an exercise workout (zero to 30 minutes prior); and after the workout (one to two hours and before a snack). If desired, these can similarly be recorded on the record pad 24. Adjustments can be made in the position of the nitrogen balance conversion sticker 28 as more information is compiled. The conversion sticker has a "sticky-back" that permits the strip to be repeatedly repositioned.

Finally, after the trainee has determined a reliably personal baseline, the trainee can engage in a Phase 3 maintenance program where the urine is tested only before workout (zero to 30 minutes prior); and after workout (one to two hours and before a snack).

As shown in FIG. 5 an indicator stick or detection wand for ketones is shown and designated generally by the reference numeral 50. The stick 50 is similarly fabricated from a plastic strip 52 with a first reagent zone 54 at one end having a chemical reagent 56 thereon that reacts with urine to indicate the level of ketones, primarily acetoacetic acid, in the urine. In the stick 50 shown, there is also included an adjacent reagent zone 58 having the chemical reagent 16 that reacts with urine nitrogen to simultaneously indicate the level of nitrogen in the urine. The chemical reagent 16 is as previously described for the nitrogen level test stick 10, and may be used in a combined procedure for obtaining more accurate results as to the effectiveness of a physical training or weight loss program than either test alone.

The reagent 56 consists of 7% sodium nitroprusside with 8% glycine in an 85% buffer of 10% lactose and 75% disodium phosphate. The reagent provides a reaction with ketone bodies, (acetoacetic acid and acetone) to provide color change in the indicator zone from pink to maroon on varying degrees of positive detection. The reagent composition is formulated for the indicator coloration to mature at the same time that coloration for the nitrogen test matures (120 seconds) for simultaneous reading.

Since the most accurate nitrogen balance procedure compares nitrogen intake with nitrogen loss, a program that records and quantifies the useable nitrogen in the form of useable protein in a dietary plan, and records and quantifies the nitrogen loss in the form of urine nitrogen plus an acceptable estimate of loss from the other avenues noted, will reasonably determine nitrogen balance. Similarly, a program that controls a diet and records and quantifies ketone bodies in the urine reasonably indicates the fat loss. By employing a predetermined, consistent low-fat dietary program that delivers a constant daily calorie and protein consumption and measuring the quantity of urine produced and the level of nitrogen and ketone bodies in regular periodic tests, a reasonably accurate picture of the quantitative state of nitrogen balance, and the effectiveness of a dietary and training program on fat loss is obtained. The use of a single test stick with multiple reagent zone assists in correlating test results and reducing aberrations from inconsistent procedures. A more accurate personal baseline can be established with this method because of the greater control of parameters.

The use of the controlled diet system to self-test the urine to determine nitrogen content and establish the trainee's status on an anabolic/catabolic spectrum provides an even more accurate quantitative basis that then the earlier described profile the base line profile for modifying the trainee's dietary and workout programs to maximize the utilization of intake protein and minimize the dangers of a catabolic state from excess intense training. The athlete is provided with a means for determining whether his diet is a proper balance of protein and carbohydrates, whether the athlete is wasting intake protein by overconsumption of protein and whether the desired anabolic level is being maintained.

Because of the availability of protein supplements with an accurately determined useable protein content, variations in diet using such supplements can assist in determining a reliable baseline under varying training conditions, and can be used to quantitatively adjust protein intake to accommodate for such future variations in the trainee's physical exercise program. Similarly, the availability of other nutritional supplements of quantified content suggest use of a similar urine test strip tests to determine excess or deficiency in other nutritional substances detectable in the urine. Such auxiliary test utilizes a secondary reagent zone 32 on the nitrogen indicator stick 10 or a third reagent zone 60 on the modified combination stick 62 shown in FIG. 6 with a reagent that reacts to the nutritional substance, product of the nutritional substance, or other agent in the urine.

Ordinarily, where an individual desires to lose fat without loss of muscle or to lose fat and gain muscle, close attention is directed at diet. While a varietal diet can be maintained with an effort to reduce fat, oil and sugar intake while recording estimated usable protein, it is more effective to establish a protein balance level when following a predetermined dietary program. In this manner, a more accurate calculation of protein intake can be derived. By conscious planning a constant daily protein intake can be devised as a dietary standard. This is particularly useful in gathering group statistics for approximating generic standards for personal comparison. However, of greater importance is the advantage in minimizing variables for increasing the accuracy of averaged, periodic tests. Reasonably accurate quantitative results can be obtained for daily urine nitrogen/ketone discharge by measuring daily volumes of urine and periodically testing the urine for nitrogen and ketones, one or more times during the day.

The tests are best performed with the combination sticks 50 and 62. A spot reading can be effected using a double color chart card 64, as shown in FIG. 7, having a color scale 66, preferably yellow to dark blue green, with representative indicia 68 corresponding to the measure of urine nitrogen in milligrams per deciliter. An approximate nitrogen balance scale 70, with indicia 72 adjusted to more accurately represent the protein excess or deficiency in grams per day for a user with a supplemented or high protein diet with a regular exercise program. Normally, the tests should indicate a positive protein state with variations resulting from variations in the workout regimen.

The double color chart card 64 also includes a color scale 74, preferably from pink to maroon to reduce the chance of confusion with the nitrogen test, for ketone tests. The ketone color scale 74 has representative indicion 76 corresponding to the measure of urine ketone bodies in milligrams per deciliter. An interpretive scale 78 indicates whether the approximate ketone discharge level is low, indicating an ineffective diet and exercise program; neutral, indicating a normal level of discharge; high, indicating an effective diet and exercise program, or danger, indicating an excessive loss where factors other than a healthy diet and exercise program are contributing to an unhealthy condition. As medical and nutritional studies advance, a more accurate definition can be applied to the translated meaning of quantitative ketone measurements, for example how many grams of body fat loss the ketone discharge represents. Ideally, the protein balance should indicate an anabolic or positive protein state with neutral or high ketone loss depending on the current condition of the user the intent to lose fat or maintain current fat levels in a strength or muscle gain program.

As an alternative to the color block cards 18 and 64, test results can be correlated to a useable indicator by a color wheels 80, as shown in FIG. 8 and 9. The color wheel enables convenient factoring of the total urine discharge into the nitrogen and ketone level measurements for a more accurate quantitative determination of daily nitrogen discharge and ketone discharge in urine.

Using the more complex protein wheel assembly 82, a determination of nitrogen balance in a form that translates to grams of protein above a balance or grams of protein below a balance can be estimated. While this measurement is not one used in medical journals or scientific studies, it is practical for the ordinary dieter or athletic trainee as it translates to protein consumption. Where the result is negative ten grams of protein, the user realizes at least ten grams of useable protein must be consumed just to achieve a balance under current conditions. Although useable protein is determined by a protein efficiency ratio, where typically from 70-95% of dietary protein is useable, depending on source, for example, plant or animal, the diet conscious user can easily make the necessary overconsumptions necessary to achieve a balance or an anabolic state using readily available food charts or special protein supplements.

The protein wheel 80 has an outer disk 84 divided into color sectors 86 indicative of nitrogen content in the urine in milligrams per deciliter. An inner disk 88, having a common axis pin 90 for rotation relative to the outer disk, has sectors 92 indicative of the total measured urine loss in milliliters per day. A hidden disk 94 has a series of numbers 98 indicative of grams of protein, plus and minus. The hidden disk 94 has an indicator pointer 100 that points to a series of numbers 102 representing protein intake in grams/day. Shifting the pointer shifts the hidden disk.

To operate, a urine test is made with the nitrogen stick to generate a color representing the nitrogen content of the sampled urine. The color sector corresponding to the color of the reacted reagent zone is selected. The sector of the inner disk 88 representing the previous 24 hour urine quantity (including the sampled quantity) is rotated to align with the selected color sector. The indicator arrow 100 is set on zero to reveal the equivalent grams of protein lost in the pertinent sector window. These representing figures are adjusted to include approximations for losses by other avenues such as sweat, hair loss, etc. By shifting the indicator arrow 100 to point at the figure representing the quantity in grams of protein consumed in the past 24 hours, the net protein loss or gain will appear in the pertinent sector window.

The color sectors include numerical indicia 104 representing nitrogen loss in milliliter per decaliter to enable a number of periodic tests to be performed during a 24 hour period. The numerical test results are easily averaged to determine an averaged color sector to be used in calculating the net protein loss or gain.

Using a separate color wheel, or preferably the obverse side of the color wheel 80 of FIG. 8 the relative ketone level can be determined quantitatively. The ketone wheel assembly 82 is somewhat simpler than the protein wheel assembly and includes an outer disk 108 divided into sectors 110 of different color ranging from buff pink to dark maroon. The colors correspond to the range of colors of the ketone reagent 56 on the ketone sticks 50 and 62. The color sectors 110 have numerical indicia 112 representing the level of ketones in the tested urine sample in milligrams per day.

An inner disk 114 has sectors 116 with indicia 118 representing the total urine loss as measured in a day in milliliters per day. The inner dish 114 is similar to the inner disk of 88 of the protein wheel assembly. The sector of the innerdisk representing the user's total urine discharge for the past 24 hours is selected and aligned with the color sector 110 of the outer disk representing the tested ketone content of the urine or preferably the average of multiple tests periodically in the day. The total ketone loss in the day is revealed in the pertinent window 122 of the inner disk 114 by numerical indicia 124 representing milligrams.

The window can also reveal a color series, such as yellow, green, blue and red with text indicia 126 for below average, average heavy and danger, respectively.

As noted, as studies improve understanding of the precise correlation of ketone loss with fat metabolism, both in food and from the body, a more meaningful and definitive relationship of ketone level and body fat loss will be representatively incorporated into the ketone wheel assembly.

Naturally, where either a ketone test stick or nitrogen test stick is used in a dietary program alone, a separate wheel is used for each separate test. The combination wheel shown for reasons of cost and compactness, is preferred for use with the combination sticks of FIGS. 5 and 6.

Figure 3:
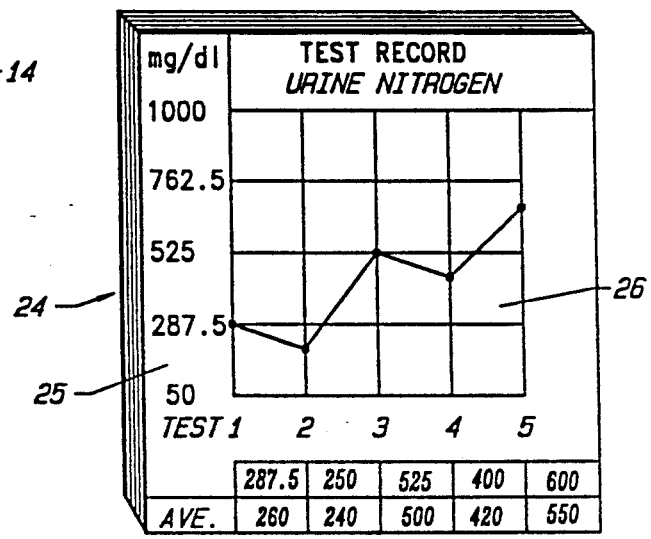
FIG. 3 is a plan view of a test record pad.

For improved results a five day regimen having a controlled diet that is constant in caloric and protein content is combined with a consistent moderate exercise program. Daily urine discharge is measured and periodic tests with the test strips are preformed. Because of the controlled diet wild variations should not occur unless there is a defect in the test items or special condition in the user that warrants concern. Spaced tests, but not necessarily at the exact same time are preferred to minimize eccentric fluctuations. At least three of the five days should be tested. The results are recorded on a note pad of the type of FIG. 3 and 4 or on an extended wall chart 130 as shown in FIG. 10 to track multiple daily results such as protein intake urinary nitrogen discharge 134, ketone discharge 136 and effective plus or minus nitrogen balance 138. Other graph lines can be added as additional nutritional correlations become available for inexpensive self-administered testing.

Although the term trainee is used herein, it is to be understood that this term includes animals, as well as humans, and dieters as well as athletes.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A personal method of determining qualitative nitrogen balance and fat loss for use in a training or dietary program of a trainee comprising the steps of:
    (1) testing the urine of the trainee with a personal test kit with a non-invasive indicator means having a reactant for detecting and indicating the level of nitrogen in the tested urine,
    (2) repeating the testing at spaced intervals in accordance with a predefined, repetitive procedure during a pretraining or moderated training program,
    (3) averaging the resulting urine nitrogen levels from the repetitive testing step and establishing a personal nitrogen baseline for the trainee,
    (4) testing the urine of the trainee periodically during a health regimen to determine the nitrogen level in the trainee's urine after each test,
    (5) comparing the nitrogen level of the trainee during the health regimen to the baseline,
    (6) determining the relative nitrogen balance from the degree variation of the tested level during the health regimen from the established, personal baseline,
    (7) testing the urine of the trainee with a personal test kit with a non-invasive indicator means having a reactant for detecting and indicating the level of ketones in the tested urine,
    (8) repeating the testing at spaced intervals in accordance with a predefined repetitive procedure during a prediet program,
    (9) averaging the resulting urine ketone levels from the repetitive testing and establishing a personal ketone baseline for the trainee,
    (10) testing the urine of the trainee periodically during the health regimen to determine the ketone level in the trainee's urine after each test,
    (11) determining the effectiveness of the program for fat loss by comparing the ketone level during the health regimen with the baseline.

2. The method of claim 1 comprising the further steps of:
   (1) maintaining a diet having a constant daily protein and calorie content for a defined number of days during the moderated training program,
   (2) measuring the quantity of daily urine discharge;
   (3) calculating the approximate quantitative daily nitrogen loss from urine discharge, using the nitrogen levels from multiple urinary tests averaged daily for estimating a total daily urine nitrogen discharge baseline.

3. The method of claim 2 wherein a nitrogen intake in the form of dietary protein is preselected together with an exercise program to produce a daily nitrogen discharge approximated from the total daily urine nitrogen discharge that is balanced or represents a moderate anabolic state to establish a reasonably healthy adjusted baseline.

4. The method of claim 2 comprising the further step of:
   converting the degree of variation of the calculated quantitive daily nitrogen loss from urine discharge relative to the daily urine nitrogen discharge baseline to determine an effective daily protein quantity deficiency or surplus.

5. A personal method of determining qualitative fat loss, comprising the steps of:
   (1) testing the urine of a trainee with a personal test kit with a non-invasive indicator means having a reactant for detecting and indicating the level of ketones in the tested urine,
   (2) repeating the testing at spaced intervals in accordance with a predefined repetitive procedure during a prediet program,
   (3) averaging the resulting urine ketone levels from the repetitive testing and establishing a personal ketone baseline for the trainee,
   (4) testing the urine of the trainee periodically during a health regimen to determine the ketone level in the trainee's urine after each test,
   (5) determining the effectiveness of the regimen for fat loss by comparing the ketone level during the health regimen with the baseline.

* * * * *